United States Patent
Moran et al.

(10) Patent No.: US 8,920,645 B2
(45) Date of Patent: Dec. 30, 2014

(54) DISPOSABLE CHROMATOGRAPHY VALVES AND SYSTEM

(75) Inventors: Michael G. Moran, Danville, NH (US); Scott P. Fulton, Middleton, WI (US)

(73) Assignee: Tarpon Biosystems Inc., Marlborough, MA (US)

( * ) Notice: Subject to any disclaimer, the term of this patent is extended or adjusted under 35 U.S.C. 154(b) by 2353 days.

(21) Appl. No.: 11/567,970

(22) Filed: Dec. 7, 2006

(65) Prior Publication Data

US 2007/0131615 A1 Jun. 14, 2007

Related U.S. Application Data

(60) Provisional application No. 60/748,260, filed on Dec. 7, 2005.

(51) Int. Cl.
| | |
|---|---|
| *G01N 30/20* | (2006.01) |
| *F16K 7/12* | (2006.01) |
| *F16K 27/00* | (2006.01) |
| *F16K 31/06* | (2006.01) |
| *B01D 15/14* | (2006.01) |
| *B01D 15/18* | (2006.01) |
| *G01N 30/46* | (2006.01) |

(52) U.S. Cl.
CPC ............... *F16K 7/126* (2013.01); *F16K 27/003* (2013.01); *B01D 15/14* (2013.01); *G01N 30/20* (2013.01); *B01D 15/1864* (2013.01); *B01D 15/1821* (2013.01); *F16K 31/06* (2013.01); *G01N 30/468* (2013.01); *G01N 2030/205* (2013.01)
USPC ..................... 210/198.2; 210/656; 251/129.01

(58) Field of Classification Search
CPC ....... F16K 7/126; F16K 31/06; F16K 27/003; G01N 30/20; G01N 30/468; G01N 2030/205; B01D 15/14; B01D 15/1821; B01D 15/1864
USPC ........... 210/198.2, 635, 656, 424; 251/129.01
See application file for complete search history.

(56) References Cited

U.S. PATENT DOCUMENTS

| | | | | |
|---|---|---|---|---|
| 3,922,223 | A | * | 11/1975 | Burkhartsmeier ......... 210/198.2 |
| 3,926,809 | A | * | 12/1975 | Jones ......................... 210/198.2 |
| 4,155,846 | A | * | 5/1979 | Novak et al. .................. 210/659 |
| 4,364,263 | A | * | 12/1982 | Sankoorikal et al. ........ 73/61.56 |

(Continued)

FOREIGN PATENT DOCUMENTS

| | | |
|---|---|---|
| EP | 1003036 A1 | 12/1999 |
| EP | 1178308 A1 | 5/2001 |

(Continued)

*Primary Examiner* — Ernest G Therkorn
(74) *Attorney, Agent, or Firm* — Joseph T. Leone, Esq.; DeWitt Ross & Stevens S.C.

(57) ABSTRACT

Described is a disposable valve that includes an actuation layer operationally linked to a flexible diaphragm; a valving layer operationally linked to the flexible diaphragm; and a connection layer operationally connected to the valving layer; wherein the valving layer and the connection layer have a corresponding plurality of channels passing therethrough, and the channels define at least one fluid flow path, and the flexible diaphragm is movable between a first open position wherein fluid can flow through the fluid flow path, and a second closed position wherein fluid cannot flow through the fluid flow path. Chromatographic systems incorporating a plurality of such valves, optionally integrated into a unitary valve block, are also described.

6 Claims, 4 Drawing Sheets

(56) References Cited

U.S. PATENT DOCUMENTS

| | | | |
|---|---|---|---|
| 4,581,624 A | 4/1986 | O'Connor | |
| 4,629,561 A * | 12/1986 | Shirato et al. | 210/198.2 |
| 4,840,730 A * | 6/1989 | Saxena | 210/198.2 |
| 4,848,722 A | 7/1989 | Webster | |
| 4,900,446 A * | 2/1990 | Anderson | 210/657 |
| 4,917,575 A * | 4/1990 | Miller et al. | 417/52 |
| 4,935,040 A * | 6/1990 | Goedert | 73/23.22 |
| 5,004,547 A * | 4/1991 | Grunfeld et al. | 210/635 |
| 5,089,124 A * | 2/1992 | Mahar et al. | 210/198.2 |
| 5,176,359 A | 1/1993 | Leveson et al. | |
| 5,203,368 A | 4/1993 | Barstow et al. | |
| 5,470,464 A | 11/1995 | Priegnitz | |
| 6,019,897 A * | 2/2000 | Horsman et al. | 210/198.2 |
| 6,063,284 A | 5/2000 | Grill | |
| 6,318,157 B1 * | 11/2001 | Corso et al. | 73/61.52 |
| 6,331,250 B1 | 12/2001 | Kaneko et al. | |
| 6,544,413 B1 | 4/2003 | Nagamatsu et al. | |
| 6,641,783 B1 * | 11/2003 | Pidgeon et al. | 422/70 |
| 6,743,356 B1 * | 6/2004 | Fermier et al. | 210/198.2 |
| 6,911,151 B1 * | 6/2005 | Muller-Kuhrt et al. | 210/656 |
| 7,217,367 B2 * | 5/2007 | Huang et al. | 210/656 |
| 7,514,000 B2 * | 4/2009 | Gilbert et al. | 210/635 |
| 2002/0020670 A1 * | 2/2002 | Petro | 210/656 |
| 2002/0088754 A1 | 7/2002 | Tanimura et al. | |
| 2002/0164816 A1 * | 11/2002 | Quake | 436/161 |
| 2003/0230521 A1 * | 12/2003 | Schick | 210/110 |
| 2005/0000900 A1 * | 1/2005 | Huang et al. | 210/656 |
| 2005/0269264 A1 * | 12/2005 | Fermier et al. | 210/635 |
| 2007/0254278 A1 * | 11/2007 | DeSimone et al. | 435/5 |
| 2008/0264863 A1 * | 10/2008 | Quake et al. | 210/651 |

FOREIGN PATENT DOCUMENTS

| | | |
|---|---|---|
| EP | 1336610 A1 | 5/2002 |
| EP | 1873520 A1 | 9/2006 |
| JP | H3-13452 | 6/1991 |

\* cited by examiner

14 Actuation Layer

12 Valving Layer

10 Connection Layer

A

B

DISPOSABLE CHROMATOGRAPHY VALVES AND SYSTEM

CROSS-REFERENCE TO RELATED APPLICATIONS

Priority is hereby claimed to provisional application Ser. No. 60/748,260, filed Dec. 7, 2005, which is incorporated herein by reference.

BACKGROUND OF THE INVENTION

Liquid chromatography is very widely used for producing biopharmaceuticals, particularly for purifying a product molecule following its expression by fermentation, in cell culture, via transgenic plants or animals, or other means. A range of different modes of chromatographic separation are used, including ion exchange, hydrophobic interaction, size exclusion, affinity, metal chelate, reversed-phase chromatography, etc., often with more than one mode used in a sequence of stages in a given process. In each stage, a cycle of steps is run on a column filled with a particular chromatographic packing. These steps include loading of the feed solution, followed by a sequence of various solutions of different pH, ionic strength and/or concentrations of solvents, chaotropic agents, detergents, or specific eluent or cleaning agents. These steps are typically run in a semi-batch manner, usually including one or more feed, wash, elute, clean, and equilibrate steps. The cycle of steps is usually repeated multiple times with the same column and packing until the entire batch of product has been processed. At the completion of a batch the entire system is carefully cleaned and the column is either stored for reuse in another batch or the packing is discarded.

The use of chromatography for biopharmaceutical purification and production has a number of important challenges. One is that the separation system must be very extensively cleaned and the cleaning protocol must be capable of being validated. Cleaning before use is necessary to remove any residual contaminants from the assembly of the system and the packing of the column. During the batch, cleaning is needed to insure that the column and system are in an equivalent state at the beginning of each cycle. Cleaning before storage between batches is particularly critical to preserve batch-to-batch equivalence and to prevent the growth of microorganisms that could destroy the packing and contaminate later batches. If the equipment is to be reused for a different product, it must be completely cleaned of all traces of prior product to prevent cross-contamination. Sometimes the costs of cleaning procedures, the materials involved (such as very expensive high purity water) and the associated testing and documentation required for validation can exceed the costs associated with the process itself. This is particularly problematic for early-stage clinical production, where only a few relatively small batches may be made.

In recent years there has been a growing demand not only for larger annual amounts of some biopharmaceutical products but also for available production facilities to make an ever-greater number of products. As a result of these pressures a great deal of effort has been put into increasing the expression levels of the various recombinant production systems used to manufacture biopharmaceutical proteins, peptides and other products. The outcome has been a continuing and dramatic improvement in the productivity of bioreactors and other production facilities. The increased output has been a major benefit, both for the industry and for the consumers.

However, the increased quantities of product to be processed in each batch have created a major challenge for the chromatography systems used for downstream purification. With conventional technology, the systems must be made larger to handle the increased amount of product in the same time span. However, if the total annual production of product has not increased, the number of cycles over which the expensive chromatography packings are used is decreased, thereby driving up production costs significantly. That is, the same amount of total product is made in far few batches. As a result, the capital investment made in the chromatography equipment is not utilized efficiently because the equipment itself is not utilized to its full capacity. In addition, in some cases the size of the column is already at or near the practical limits, especially for systems that must be designed for validated cleaning. Simply enlarging the present chromatography systems is not a practical option.

One increasing trend in the biopharmaceutical industry is to use disposable process systems and components. Disposable systems eliminate the need for much of the cleaning process and the validation and testing associated with it because the systems can be produced pre-cleaned and pre-sterilized and are then discarded once the batch is completed. Plastic bags and tubing sets are now widely used in a variety of applications for solution and media preparation and storage, and increasingly sophisticated disposable units are being developed for use as bioreactors, mixers, fill/finish systems, etc.

The adoption of disposable systems for chromatography has been hampered by a number of factors. One is that the columns themselves must provide a number of key functions, including packing, flow distribution across the bed, pressure containment and aseptic operation. Although small, pre-packed columns, such as those widely used in laboratory applications, might be made inexpensively enough to be disposable, this approach would not be cost-effective for the large-volume columns (sometimes several hundred liters) used for production-scale purification. In addition to the columns, however, the rest of the chromatography system (including the significant number of valves, pumps and detectors) must also be made fully disposable (at least for the parts contacted by the process stream) in order for the benefits of disposability to be realized fully.

In the chemical industry, the challenge of very large scale chromatographic separation has been met through the use of multiple-column systems (including so-called simulated moving bed or SMB systems), in which a number of identical columns are connected together through a set of valves and pumps. Often these systems are configured so that some of the columns are engaged in loading the feedstream, while others are engaged in other parts of the process. At certain points in the process the valve positions and the consequent steps in which each of the columns are engaged are changed. These systems can be set up to run in a semi-continuous cycle, with all steps of the separation cycle taking part simultaneously on different columns in the system.

In addition to the use of smaller, more practical columns and continuous operation, multiple column systems have additional benefits. The effective capacity of the chromatographic packing can be higher because the elution process is only performed on a column that is completely loaded with product. In addition, proper design of the process can result in significantly reduced consumption of reagents per unit of product produced.

Multiple column systems have not been used significantly in biopharmaceutical production for several reasons. One reason is that some of valves used in these systems make it difficult or impossible to maintain the internal aseptic conditions required for biopharmaceutical production. More importantly, the large number of valves, pumps and other components presents a major challenge for cleaning and validation, both of which are critical and legally required steps in biopharmaceutical production.

SUMMARY OF THE INVENTION

The present invention is summarized as a disposable chromatography system, comprising disposable pre-packed columns and a disposable plumbing system. In one aspect, the invention provides a plumbing system with a disposable process fluid contact portion and a reusable actuator portion.

In another aspect, the plumbing system comprises modular valves, each containing a disposable process fluid contact portion and a reusable actuator portion. The two portions may be manufactured together as a single unit or sold separately and assembled by a middleman or end user to form a valve train for use in the chromatography system.

In another aspect, the disposable fluid contact portion contains a flexible element in contact with a reusable actuator portion. The flexible element is preferably in the form of a tube, diaphragm or membrane, with the actuator acting upon the flexible element to provide valve switching action (i.e. continuously adjustable, full-open to full-closed).

In another aspect, the modular valve comprises a connection layer, a valving layer and an actuation layer, each on a separate plane (preferably substantially parallel with one another, although other configurations are within the scope of the invention), with the valving layer and the actuation layer separated by a flexible diaphragm or membrane. The connections between the layers are sealed to enable aseptic operation and the fluid paths are designed and configured for complete cleaning and validation.

In another aspect, the modular valves are assembled together with disposable tubing installed in one or more peristaltic-type pumps, optionally in combination with disposable detector flow cell modules, a reusable detector system to measure optical absorbance, pH, conductivity, etc., and/or disposable, pre-packed columns to form a chromatography system with a completely disposable process fluid contact portion and a reusable actuator portion.

In another aspect, the modular valves, other disposable and reusable system components and disposable columns are assembled together with a suitable control system (such as a microprocessor-controlled, programmable computer) able to actuate each system element independently to form a multi-column chromatography system with a completely disposable process fluid contact portion and a reusable actuator portion.

Thus, one version of the invention is a valve comprising an actuation layer operationally linked to a flexible diaphragm; a valving layer operationally linked to the flexible diaphragm; and a connection layer operationally connected to the valving layer. The valving layer and the connection layer have a corresponding plurality of channels passing therethrough, wherein the channels define at least one fluid flow path, and wherein the flexible diaphragm is movable between a first open position wherein fluid can flow through the fluid flow path, and a second closed position wherein fluid cannot flow through the fluid flow path.

Another version of the invention is the valve described in the immediately preceding paragraph operationally connected to an actuator. The actuator is operationally connected to the flexible diaphragm, wherein the actuator is dimensioned and configured to move the flexible diaphragm between the open position and the closed position.

The invention is further directed to a liquid chromatography system comprising: a valve as recited herein, operationally linked to a peristaltic pump. Preferably the system further comprises at least one chromatography column operationally linked to the valve, and preferably further comprises a detector operationally linked to the column. The system may also include a user-programmable controller dimensioned and configured to control operation of the valve, the pump, and the detector. The system may also include a plurality of chromatography columns.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

The terms "operationally linked" or "connected" denote that the referenced elements function as described with respect to one another. The referenced elements need not be physically touching, or otherwise directly linked one to the other in order to be considered operationally linked or connected. There may be intervening elements so long as the elements referenced as operationally linked or connected function as described.

Other objects, advantages and features of the present invention will become apparent from the following specification taken in conjunction with the accompanying drawings.

BRIEF DESCRIPTION OF THE DRAWINGS

FIG. 2A shows the actuator depressurized (valve opened); FIG. 2B shows the actuator pressurized (valve closed).

DETAILED DESCRIPTION OF THE INVENTION

Figure 1A:
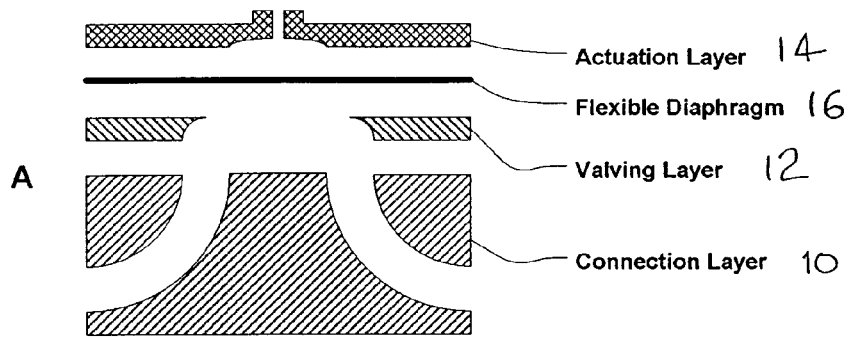
FIG. 1A shows an exploded cross-sectional view of the different layers of the disposable fluid contact portion of the modular valve of the present invention.

The present invention relates to an improved system for liquid chromatography. The system is particularly suited for use in the production of biopharmaceuticals, but can be used in any field requiring the use of liquid chromatographic purification or separation. The improved system is designed to make it practical for all of the fluid-contacting portions of the system to be disposable and to make it practical to use multi-column systems for biopharmaceutical production.

All liquid chromatography systems include a column containing a suitable amount of packing material in a bed (generally cylindrical in shape) contained within a tube having suitable flow distribution elements on either end to spread liquid entering or leaving the column through tubes evenly across the bed. The walls and ends of the column must be sealed to prevent leakage of process liquid to the outside and must be able resist the pressure caused by the flow of liquid through the bed. For biopharmaceutical production specifically, the column must be made of suitable materials with a smooth surface finish and a proper seal design to enable complete cleaning and prevent entrapment of microorganisms and other contaminants within the column.

Packing columns to enable good chromatographic performance can be very tricky and may require special equipment or skills. (In the industry, packing columns to yield clean separations is a notoriously troublesome operation that is not easily systematized.) As columns become larger in volume, the difficulty and practical challenges of efficient packing tend to increase. When the design requirements for the column itself and the special equipment needed for packing (and unpacking) are considered, large process columns for biopharmaceutical production can be very expensive.

In addition to the column, chromatography systems must have a pump to provide operating pressure and precise control of the flow rate through the column. Systems also have a number of valves to control which of the many different solutions (feed, wash buffer, eluent, etc.) is being fed to the column, and whether the effluent is being collected as product or sent to waste. Systems also generally require some flow-through detectors, usually including optical (UV) absorbance detectors and often pH and conductivity detectors.

To obtain the benefits of using disposable technology for chromatographic processes, it is necessary to make all of the elements of the chromatography system which contact the process fluids—columns, pumps, valves and detector flow cells—disposable. Each of these elements must be considered for the entire system to work.

Disposable pre-packed columns are widely used in the laboratory field, and the same technology can be adopted for process applications. By supplying the column already packed, tested, cleaned and sanitized (or possibly sterilized), all of the difficulty, special equipment and skill needed to pack the column is transferred from the end-user to a specialized manufacturer/vendor. In essence, the end-user purchases a column that is ready to be used without further assembly.

Peristaltic-type pumps have been widely used throughout biopharmaceutical manufacturing, including for chromatography. The fluid contact portion of the pump is a flexible tube (made from silicone rubber or similar materials), which may be easily replaced within the pump drive.

Fabricating a disposable valve presents a more daunting challenge. Typically a permanent valve has a fluid contact portion which must be isolated from the actuator of the valve. Generally, these are manufactured as a single unit and are installed as fixed components in a system. A key aspect of the present invention is a design for a modular valve in which the fluid contact portions and the actuator portions are separable, with the actuator portions being part of the fixed system and the fluid contact portions being disposable. When the various portions are operationally linked to one another, the unit functions as a valve. When the project is complete, the fluid contact portions of the valve are disconnected and discarded. The remaining portions are saved for reuse.

Figure 1B:
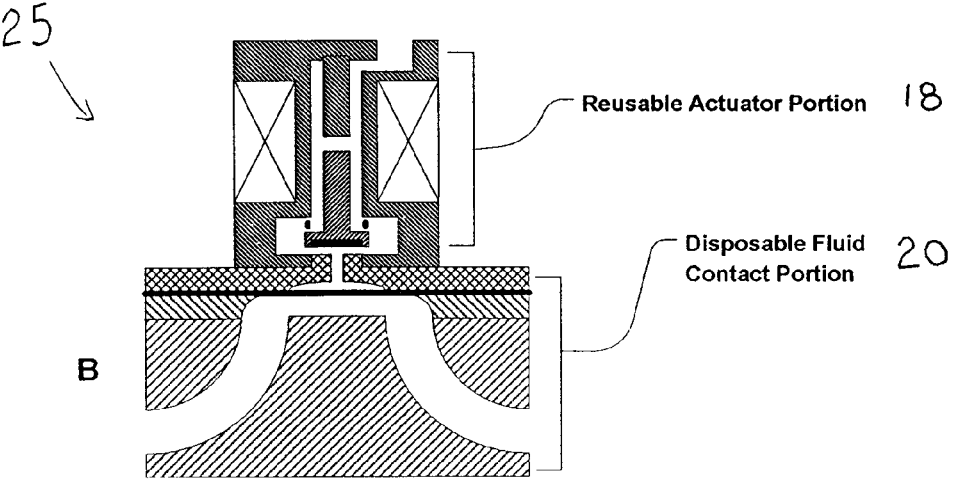
FIG. 1B shows a cross-section of the assembled modular valve shown in FIG. 1A, in combination with a disposable fluid contact portion and the reusable actuator portion (pneumatic actuation).

FIGS. 1A and 1B shows a cross-sectional view of such a valve. The disposable fluid contact portion 20, shown in exploded cross-section in FIG. 1A, is composed of three main layers: a connection layer 10 (for making the fluid connections within the system); a valving layer 12 (where the actual fluid flow switching takes place); and an actuation layer 14 (which provides the switching mechanism). The actuation layer 14 and the valving layer 12 are separated by a flexible diaphragm 16 (preferably made of silicone rubber, but which can be fabricated from any suitably flexible, impervious material that is compatible with the product and the various process solutions). The actuation, valving, and connection layers may be economically manufactured of plastic materials (preferred) or any other suitably stiff material compatible with the product and the various process solutions (e.g., glass, metal, ceramics, composites, etc.) Where the layers are made of plastic, they can be fabricated via injection molding or via high throughput machining operations. The parts can be assembled to form individual valves or they can be operationally linked to form complex valve blocks (as described below).

FIG. 1B shows an assembled modular valve 25, with a reusable actuator portion 18 connected to the disposable fluid contact portion 20. As shown in FIG. 1B, the actuator is a pneumatic valve (preferred), with the actuation provided by air pressure acting on the flexible diaphragm. Other actuators may also be used, including hydraulic, electronic, piezoelectric, and/or mechanical actuators.

Figure 2A:
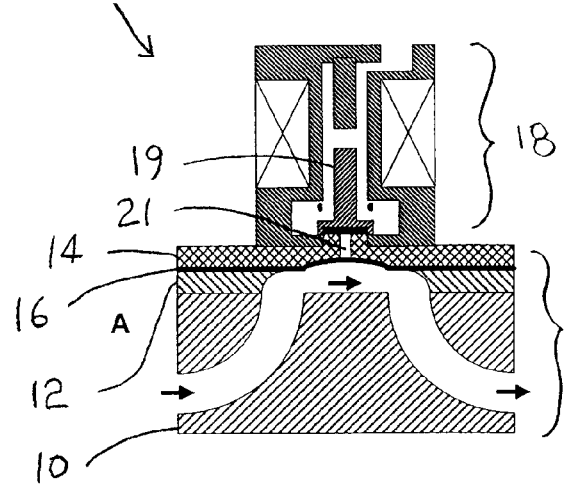
FIGS. 2A and 2B show cross-sectional views of the modular valve depicted in FIG. 1B.
Figure 2B:
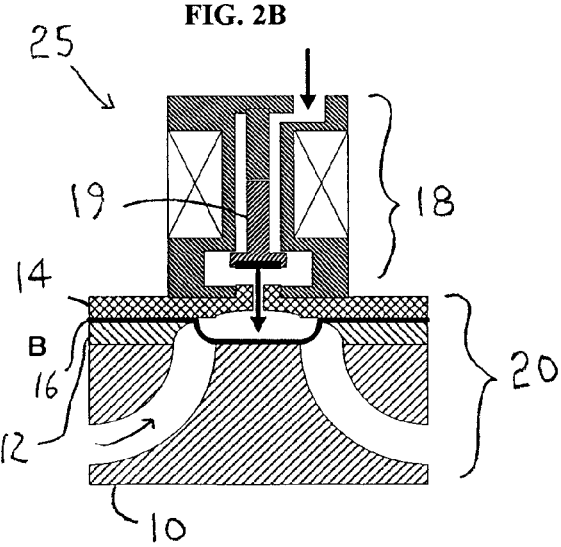

FIGS. 2A and 2B show the basic operation of the modular valve according to the present invention. In FIG. 2A the actuator valve is closed; i.e., the plunger 19 is biased against aperture 21 in the actuation layer 14. The flexible diaphragm 16 is depressurized, and the fluid channel (shown by the arrows in FIG. 2A) is open. In FIG. 2B the actuator valve is opened; i.e. the plunger 19 is withdrawn from the aperture 21 in the actuation layer 14, thus allowing air pressure to force the flexible diaphragm 16 against the connection layer 10, thereby blocking the flow of liquid through the fluid channel (shown by the arrow in FIG. 2B). The fluid channel is closed. The actuator may be a simple two-position actuator (open and closed, as shown in FIGS. 2A and 2B) or the actuator may be continuously variable between the open and closed positions. The variability is easily achieved by controlling the pressure exerted on the flexible diaphragm 16 when the actuator valve 18 is opened.

Figure 3A:
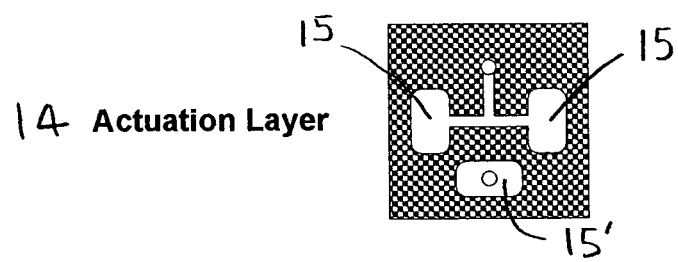
FIGS. 3A, 3B, and 3C depict top plan views of the three layers of the modular valve disposable fluid contact portion in a typical configuration for use in a multi-column system. Depicted are the actuation layer (FIG. 3A), the valving layer (FIG. 3B), and the connection layer (FIG. 3C).
Figure 3B:
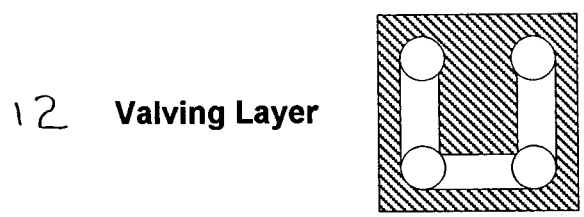
Figure 3C:
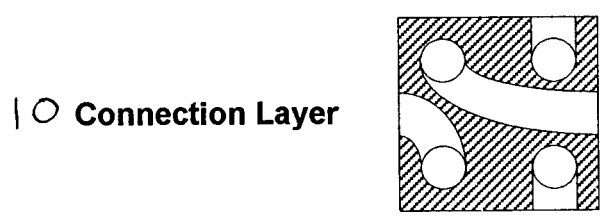

FIGS. 3A, 3B, and 3C show top plan views of the different layers of the modular valve in a typical stream switching configuration used in a multi-column system. The connection layer 10 at the bottom of the assembly (FIG. 3C) has four ports. As shown in FIG. 3C, each port is collinear with one of the other ports and at right angles to the other two. This is for purposes of illustration only. The ports may exit the connection layer in any desired geometry. The number of ports (four in the illustration) is also arbitrary. There may be more or less than four ports.

The valving layer 12 (FIG. 3B) provides several alternative channels connecting the ports defined in the connection layer 10. The actuation layer 14 (FIG. 3A) provides holes for the actuator to access specified areas of the diaphragm in order to open or close specific channels in the valving layer. As shown in FIG. 3A a pair of upper holes 15 are provided, along with a single lower hole 15' centered between the two upper holes.

Figure 4A:
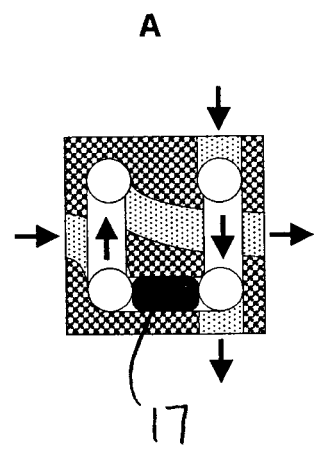
FIGS. 4A and 4B show top plan views of the assembled layers and illustrates the open position of the valve (FIG. 4A) and the closed position of the valve (FIG. 4B).
Figure 4B:
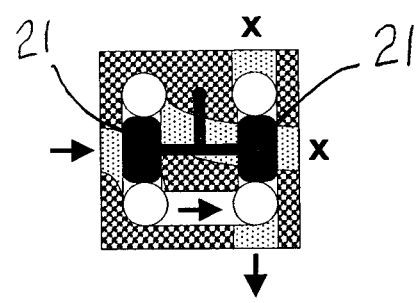

FIGS. 4A and 4B show how the particular configuration illustrated in FIGS. 3A, 3B, and 3C functions. In a first position (FIG. 4A), the lower actuator section (corresponding to hole 15' in FIG. 3A) is pressurized (depicted as a black box 17 in FIG. 4A) and the upper section is depressurized. In this configuration, the valving layer connects the two left-hand ports to each other (i.e., the upper-left and lower-left circles in FIG. 4A) and also connects the two right-hand ports to each other (i.e., the upper-right and lower-right circles in FIG. 4A). In the position shown in FIG. 4B, the upper actuator sections are pressurized (corresponding to holes 15 in FIG. 3A and depicted as black boxes 21 in FIG. 4B) and the lower section is depressurized. In this configuration, the valving layer connects two bottom ports of the connection layer (i.e., the lower-left and lower-right circles in FIG. 4B), and blocks off both of the top ports (i.e., the upper-left and upper-right circles in FIG. 4B).

Because the connection, valving and actuation layers are all on separate planes, they may each be configured independently, enabling a wide range of different valve types to be constructed. Valves may be made as individual functional modules (as shown in FIGS. 4A and 4B) which are connected together to form a system. Alternatively, multi-valve blocks can be manufactured very economically as an integrated single unit, significantly reducing the cost of disposability, as well as reducing the system volume significantly (which is important in multi-column systems).

A detector flow cell may also be made using the same concept of separating the disposable fluid contact portions from the reusable portions of the system (in this case the optics and electronics). Fiber optics may be used to construct a low-cost optical flow cell and low-cost pH and conductivity sensors may also be incorporated if needed.

Figure 5:
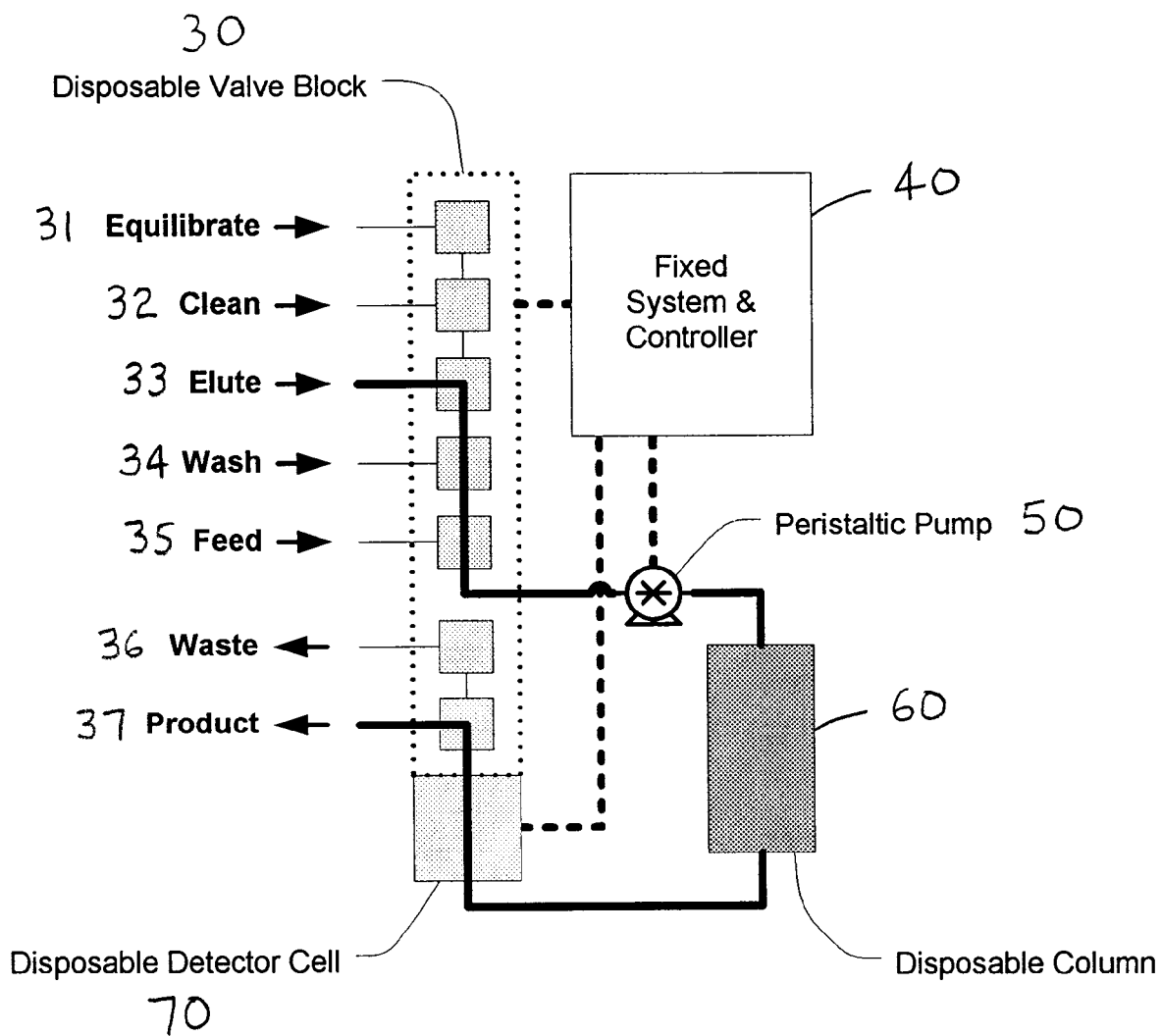
FIG. 5 is a schematic rendering showing a single column system according to the present invention. The illustrated system is assembled from a block of disposable modular valves, a peristaltic pump (with disposable pump tubing installed), a disposable column, and a disposable detector flow cell.

An illustrative and complete chromatography system according to the current invention is shown schematically in FIG. 5. The disposable valve block 30 and detector flow cell 70 are connected to their respective reusable portions, to the peristaltic pump 40, and to the control system 40. A flexible tube connecting the valve block and the column is installed in the peristaltic pump drive. A pre-packed, disposable column 60 is then connected to the system, along with containers for equilibration solution 31, cleaning solution 32, elute solution 33, wash solution 34, feed solution 35, as well as the waste collection valve 36 and product collection valve 37.

A system such as that shown in FIG. 5 can meet the needs of small-scale biopharmaceutical production, such as for clinical trial materials or for very low-dose drugs. However there is a practical limit to the size of a pre-packed column that can be manufactured inexpensively enough to be disposable and to be shipped easily from the vendor to the manufacturing site. This practical limit is considerably smaller than many of the columns used for full-scale production. In addition, it may not be practical to operate larger columns (especially if they are designed to be disposable) at higher pressures, which may be desirable for packing materials with smaller particles, or that operate at higher flow rates. Higher flows may be very useful for rapid cycling that can further enhance the process economics.

A solution to these problems is to use a multi-column system. Properly designed multi-column systems can be suitable for very large-scale production, even with columns that are of suitable size for being pre-packed, are disposable, and are amenable to operating at higher pressures. In addition, multi-column systems can have significantly higher utilization of the available binding capacity of the packing material and reduced consumption of solutions used in the process, both of which can contribute to reduced costs of production.

The challenges with adapting multi-column technology to the needs of biopharmaceutical production (including the need for rigorous, validated cleaning and for aseptic operation) can be met using the disposable modular valve system described herein. A fully operational multi-column system uses a large number of valves, which can be economically manufactured and assembled, either as individual valve modules or as integrated blocks, as described above.

Figure 6A:
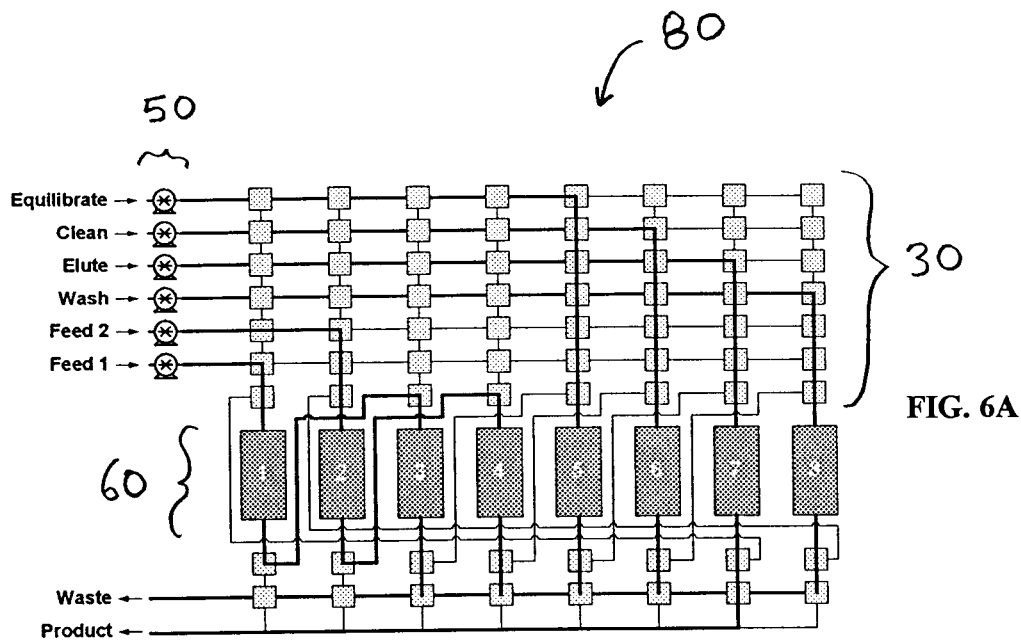
FIGS. 6A, 6B, and 6C show a multi-column system according to the present invention. Here, the system is assembled from the modular valves, disposable columns (numbered 1 to 8) and peristaltic pumps. Three distinct stages in the operating cycle are shown in FIG. 6A, FIG. 6B, and FIG. 6C (see the detailed description for full details).
Figure 6B:
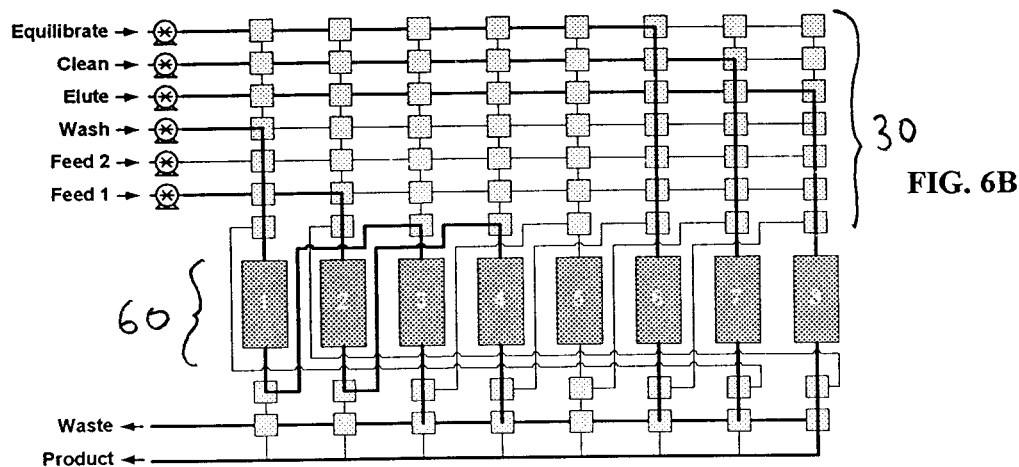
Figure 6C:
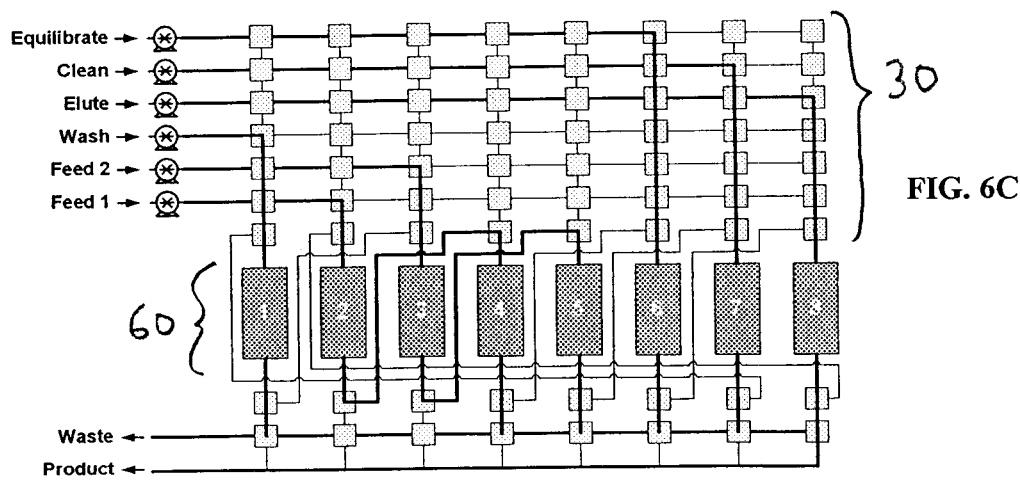

FIGS. 6A, 6B, and 6C show a schematic of such a multi-column system 80, assembled from the modular valves of the present invention. All of the steps in the process cycle are being carried out simultaneously on different columns in the system, with each input stream having its own pump 50, and corresponding valve block 30 as shown in FIG. 6A. In FIG. 6A, columns 1 & 2 within the column bank 60 are being loaded with feedstream, and their outputs are connected to columns 3 & 4, respectively, in order to capture any product that does not bind to columns 1 & 2. Because of this, column 1 can be fully saturated with product prior to washing and elution. Column 8 is being washed, column 7 is being eluted (with the output shunted to the product collection line), column 6 is being cleaned and column 5 is being re-equilibrated.

In FIG. 6B, the valves have been switched by the controller to the next position in the cycle. In FIG. 6B, column 1 is now being washed, but because it is fully saturated all of the liquid in the column is feed-containing product. The output from column 1 is therefore still shunted to column 3, which is not yet loaded. Column 2 is still being loaded, with its output being sent to column 4. Column 8 is now being eluted (with its output sent to the product collection stream). Column 7 is being cleaned and column 6 re-equilibrated. At this stage in the cycle column 5 is not active and the Feed 2 line pump is turned off.

FIG. 6C shows the next step in the cycle. The unbound product has been washed off column 1, so the output from column 1 is now sent to waste for complete washing. Columns 2 and 3 are receiving feed, with their outputs sent to columns 4 and 5, respectively. Columns 6, 7 and 8 are continuing the parts of the cycle as shown in FIG. 6B. In this fashion, a multi-column system, operationally linked using the valve assemblies according to the present invention can be used to full effect. When the project is complete, all of the columns may be disposed, along with the actuation layer, flexible diaphragm, valving layer, and connection layer.

The number of columns, process streams and outputs may be varied according to the design of the process itself and the production scale requirements. A very wide range of different process cycles may be implemented with such a system because each of the valves may be operated independently (even though they may be economically manufactured as a single unit). In addition to biopharmaceutical manufacturing, such a disposable, multi-column chromatography system can be used in any other field where cleaning is critical and costly for the reasons described above. These include, but are not limited to, the production of conventional oral pharmaceuticals, parenteral pharmaceuticals, and pharmaceutically active intermediates; high-purity chemicals for the electronics, optics, aerospace, and defense industries; materials for specialty chromatography packings, and the like.

What is claimed is:

1. A liquid chromatography system comprising:
   a valve comprising:
   an actuation layer operationally linked to a flexible diaphragm;
   a valving layer operationally linked to the flexible diaphragm; and
   a connection layer operationally connected to the valving layer; wherein the valving layer and the connection layer have a corresponding plurality of channels passing therethrough, wherein the channels define at least one fluid flow path, and wherein the flexible diaphragm is movable between a first open position wherein fluid can flow through the fluid flow path, and a second closed position wherein fluid cannot flow through the fluid flow path; the actuation layer, valving layer, and connection layer defining a disposable valve that does not include an actuator, whereby the valve may be disposed of without disposing of the actuator;

operationally linked to a peristaltic pump.

2. The liquid chromatography system as recited in claim 1, further comprising at least one chromatography column operationally linked to the valve.

3. The liquid chromatography system as recited in claim 2, further comprising a detector operationally linked to the column.

4. The liquid chromatography system as recited in claim 3, further comprising a user-programmable controller dimensioned and configured to control operation of the valve, the pump, and the detector.

5. The liquid chromatography system as recited in claim 4, further comprising a plurality of chromatography columns.

6. The liquid chromatography system as recited in claim 1, comprising a plurality of valves, each valve comprising an actuation layer operationally linked to a flexible diaphragm; a valving layer operationally linked to the flexible diaphragm; and a connection layer operationally connected to the valving layer; wherein the valving layer and the connection layer have a corresponding plurality of channels passing therethrough, wherein the channels define at least one fluid flow path, and wherein the flexible diaphragm is movable between a first open position wherein fluid can flow through the fluid flow path, and a second closed position wherein fluid cannot flow through the fluid flow path.

* * * * *